United States Patent [19]

Durand et al.

[11] Patent Number: 5,602,924

[45] Date of Patent: Feb. 11, 1997

[54] ELECTRONIC STETHESCOPE

[75] Inventors: Jocelyn Durand, Joliette; Louis-Gilles Durand, St-Jean-de-Matha; Marie-Claude Grenien, Montreal, all of Canada

[73] Assignee: Theratechnologies Inc., Montreal, Canada

[21] Appl. No.: 164,382

[22] Filed: Dec. 9, 1993

Related U.S. Application Data

[63] Continuation-in-part of Ser. No. 986,596, Dec. 7, 1992, abandoned.

[51] Int. Cl.[6] .................................................. A61B 7/04
[52] U.S. Cl. .............................. 381/67; 381/72; 381/123
[58] Field of Search ........................... 381/67, 94, 123, 381/25, 72, 74, 68.4, 104, 107, 108; 128/715

[56] References Cited

U.S. PATENT DOCUMENTS

| | | |
|---|---|---|
| 1,658,327 | 2/1928 | Dodge . |
| 2,001,537 | 5/1935 | Mason . |
| 2,340,714 | 2/1944 | Traver et al. . |
| 2,699,465 | 1/1955 | Hamilton . |
| 3,087,016 | 4/1963 | Dahl . |
| 3,182,129 | 5/1965 | Clark et al. . |
| 3,247,324 | 4/1966 | Cefaly et al. . |
| 3,311,703 | 3/1967 | Grinstead . |
| 3,455,293 | 7/1969 | Bethune . |
| 3,525,810 | 8/1970 | Adler . |
| 3,539,724 | 11/1970 | Keesee . |
| 3,555,187 | 1/1971 | Rowley . |
| 3,651,798 | 3/1972 | Egli et al. . |
| 3,772,478 | 11/1973 | McCabe et al. . |
| 3,790,712 | 2/1974 | Andries . |
| 3,846,585 | 11/1974 | Slosberg et al. . |
| 3,858,005 | 12/1974 | Marshall et al. . |
| 3,867,925 | 2/1975 | Ersek . |
| 3,989,895 | 11/1976 | O'Daniel, Sr. . |
| 4,071,694 | 1/1978 | Pfeiffer . |
| 4,072,822 | 2/1978 | Yamada . |
| 4,170,717 | 10/1979 | Walshe . |
| 4,218,584 | 8/1980 | Attenburrow . |
| 4,220,160 | 9/1980 | Kimball et al. . |

(List continued on next page.)

FOREIGN PATENT DOCUMENTS 9107532  5/1992  Germany .

OTHER PUBLICATIONS

*Kompendium Elektromedizin Grundlagen Technik*, J. Patzold, 1976 Berlin, Siemens, 1976, Phonokardiographie, see figures 4–7.

*Primary Examiner*—Curtis Kuntz
*Assistant Examiner*—Ping W. Lee
*Attorney, Agent, or Firm*—Merchant, Gould, Smith, Edell, Welter & Schmidt, P.A.

[57] ABSTRACT

The electronic stethoscope is designed to minimize the influence of the various types of noise while optimizing auscultation of the sounds of interest, and to enable a cardiologist to auscultate mechanical heart valves. It comprises a probe for sensing sounds of interest produced within a patient's body and for converting these sounds to an electric signal, and an audio amplifier and earphones for reproducing the sounds of interest in response to this electric signal. The stethoscope comprises (a) a first filter unit having a frequency response that optimizes filtering of the tremor and passing of the low frequency sound components of interest in the range including the frequencies lower than 75 Hz, (b) a second filter unit having a frequency response that optimizes both attenuation of the ambient noise and passing of the sound components of interest in the range 110–1300 Hz, taking into consideration the variation of sensitivity of the human ear in function of frequency, (c) a third filter unit for passing the sounds of mechanical heart valves, and (d) a level detector detecting the amplitude level of the electric signal to activate a pulse generator of which the pulses are applied to the audio amplifier for momentarily and repeatedly disabling this audio amplifier when the detected amplitude level is higher than a predetermined amplitude level threshold.

6 Claims, 5 Drawing Sheets

U.S. PATENT DOCUMENTS

| | | |
|---|---|---|
| 4,254,302 | 3/1981 | Walshe . |
| 4,302,627 | 11/1981 | Inoue . |
| 4,377,727 | 3/1983 | Schwalback . |
| 4,401,125 | 8/1983 | Taylor et al. . |
| 4,424,815 | 1/1984 | Kuntz . |
| 4,438,772 | 3/1984 | Slavin . |
| 4,476,436 | 10/1984 | Koizumi et al. ............ 330/10 |
| 4,498,188 | 2/1985 | Hofer . |
| 4,528,690 | 7/1985 | Sedgwick . |
| 4,534,058 | 8/1985 | Hower . |
| 4,594,731 | 6/1986 | Lewkowicz . |
| 4,598,417 | 7/1986 | Deno . |
| 4,607,643 | 8/1986 | Bell et al. . |
| 4,618,986 | 10/1986 | Hower . |
| 4,649,928 | 3/1987 | Samaras et al. . |
| 4,672,975 | 6/1987 | Sirota . |
| 4,720,866 | 1/1988 | Elias et al. . |
| 4,731,849 | 3/1988 | Bloomfield, III . |
| 4,783,813 | 11/1988 | Kempka . |
| 4,783,814 | 11/1988 | Foley . |
| 4,792,145 | 12/1988 | Eisenberg et al. . |
| 4,821,327 | 4/1989 | Furugard et al. . |
| 4,917,107 | 4/1990 | Bell et al. . |
| 4,972,841 | 11/1990 | Iguchi . |
| 4,985,925 | 1/1991 | Langberg et al. . |
| 4,991,581 | 2/1991 | Andries . |
| 5,003,605 | 3/1991 | Phillips et al. . |
| 5,010,889 | 4/1991 | Bredesen et al. . |
| 5,022,405 | 6/1991 | Hok et al. . |
| 5,025,809 | 6/1991 | Johnson et al. . |
| 5,036,543 | 7/1991 | Ueno . |
| 5,172,358 | 12/1992 | Kimura . |

ELECTRONIC STETHESCOPE

This application is a continuation-in-part of application Ser. No. 07/986,596, filed Dec. 7, 1992, now abandoned.

BACKGROUND OF THE INVENTION

1. Field of the Invention

The present invention relates to an electronic stethoscope capable of detecting and reproducing sounds of interest while eliminating most of the undesirable noise disturbing the physician or other medical practitioner during auscultation.

2. Brief Description of the Prior Art

A plurality of electronic stethoscopes have been proposed in the past. Examples are described and illustrated in the following United States patents:

| | | |
|---|---|---|
| 3,247,324 | (Cefaly et al.) | 04/19/1966 |
| 4,170,717 | (Walshe) | 10/09/1979 |
| 4,254,302 | (Walshe) | 03/03/1981 |
| 4,534,058 | (Hower) | 08/06/1985 |
| 4,594,731 | (Lewkowicz) | 06/10/1986 |

Although many electronic stethoscopes are available on the market, they have never been widely accepted by the physicians and other medical practitioners. A clinical study in different fields of the medical profession indicates that non-acceptance of the electronic stethoscopes is mainly due to the production of noise (or artefacts) disturbing the physician or other medical practitioner during auscultation as well as to the incapacity of these stethoscopes to amplify and reproduce certain biological sounds of interest. These two considerations are not redundant. Indeed, a biological sound can be either present but covered by noise, or totally absent.

Many sources of noise have been identified. These noise sources usually have a high amplitude and/or a frequency characteristic situated within the frequency range of the signal of interest whereby the quality of auscultation is substantially reduced. Of course, an efficient electronic stethoscope should be capable of processing these different sources of noise.

"Noise" is defined as being any signal other than that of interest, and can be divided into the following four categories:

A. External noise;
B. Noise related to auscultation;
C. Noise generated by the electronic circuits of the stethoscope; and
D. Noise of biological nature produced by the patient's body.

A. External noise:

This external, ambient noise is not directly connected to auscultation, but originates from the environment of the physician, the patient and the stethoscope. For example, external noise is produced by the telephone, voice, medical equipments, etc. Its frequency characteristic is situated within the range 300–3000 Hz. These acoustic waves are sensed by the electroacoustic transducer (microphone) of the stethoscope and then amplified and transmitted to the ears of the physician or other medical practitioner.

Although it is attenuated by the stethoscope probe, the external noise is still perceived by the medical practitioner as being dominant since sensitivity of the human ear is higher at ambient noise frequencies. Reference can be made to the Fletcher-Munson curves showing that a sound at a frequency of 1 kHz is perceived up to 100 times louder than a sound of same intensity at a frequency of 100 Hz. Lower sensitivity of the human ear to the low frequencies of the biological sounds results in a weaker perception thereof.

The above mentioned clinical study has determined that, amongst the various types of noise, external noise is the most disturbing. For example, the sound of a normal heart has a frequency characteristic situated within the range of 20–200 Hz and is particularly covered and affected by ambient noise. Measure of blood pressure is particularly affected by external noise since Korotkoff's sounds have low frequency characteristics.

B. Noise related to auscultation:

The three following sources of noise are associated to auscultation of a patient:

1° Noise related to the preauscultation manipulation;

2° Movements of the physician and/or patient (movements perceptible by human eyes); and 3° Tremor (involuntary trembling motion of the hand of the physician mostly imperceptible by human eyes).

1° Noise related to the preausculation manipulation:

This category includes impacts between the probe (including the electroacoustic transducer) of the stethoscope and hard objects, and the noise produced upon adjusting the different controls (switches, potentiometers, etc.) of the stethoscope. In particular, when the probe hits an object the resulting sound is sensed by the electroacoustic transducer and is then amplified to produce a very high amplitude transitory signal. Under certain circumstances, the transitory signal can have an amplitude sufficient to harm the ears of the user. Moreover, when the controls (switches, potentiometers, etc.) are mounted close to the electroacoustic transducer, adjustment thereof is susceptible to produce very unpleasant artefacts if they are not adequately isolated from the electroacoustic transducer.

2° Movements of the physician and/or patient (movements perceptible by human eyes):

Upon carrying out auscultation, noise can be generated when the physician or other medical practitioner positions and displaces the probe on the patient's body. Movement of the patient's body with respect to the probe produces the same type of noise. In both cases, the generated noise has a relatively high intensity. The power of these artefacts is surprising, in particular when the probe is positioned and then displaced on the clothes of a patient.

3° Tremor:

Considerable efforts have been made to identify and characterize the source of a low frequency rumble wrongly associated to background noise. This low frequency rumble is generated by an involuntary trembling motion of the hand of the physician or other medical practitioner during auscultation, twinned with the sensitivity of the electroacoustic pressure transducer of the stethoscope.

When the stethoscope is applied to the patient's body by a physician or other medical practitioner, a low frequency rumble is produced and superposed to the biological sounds of interest. On the contrary, the low frequency rumble disappears when the probe of the stethoscope is held on the patient's body by means of an elastic belt instead of the physician's hand. This low frequency rumble is produced by an involuntary trembling motion (tremor) of the physician's hand, which trembling motion is mostly imperceptible by human eyes and has muscular origins (positioning feedback). It is interesting to note that the low frequency rumble considerably reduces in intensity when the probe of the stethoscope is held in the air; the explanation is that an electroacoustic transducer placed in a closed space is more sensitive to variations of pressure in the cavity than to the movement itself. Of course, when the probe of the stethoscope is applied to the patient's body, the involuntary trembling motion of the hand creates variations of pressure in the air compartment between the electroacoustic transducer and the patient's body. The electroacoustic transducer senses these pressure variations and generates in response thereto a low frequency signal of which the frequency characteristic is mainly situated in the range 10–100 Hz. When held in the air, the electroacoustic transducer is subjected almost only to static atmospheric pressure whereby the rumble considerably reduces and can even disappear.

C. The noise generated by the electronic circuits of the stethoscope:

This kind of noise includes harmonic distortion caused by saturation of the electronic circuits and modifying the signal of interest, as well as residual background noise of electronic nature superposed to the signal of interest. Proper design of the electronic circuits enables this noise to be, if not completely eliminated, considerably reduced.

D. The noise of biological nature generated by the patient's body:

As defined in the foregoing description, "noise" is any signal other than that of interest. Therefore, the sounds of biological nature produced by the patient's body can be considered as being noise. Accordingly when a cardiologist auscultates a low frequency sound (for example B3 or B4 heart sounds), muscular trembling, noise generated by the intestinal peristalsis, pulmonary sounds as well as high frequency heart sounds (murmurs, mechanical heart valves, etc.) all constitute noise which disturbs his concentration.

Generally, the prior art electronic stethoscopes have a frequency bandwidth covering the ranges of frequencies of the biological sounds of interest, mentioned in the following TABLE OF COMMON AUSCULTATORY SOUNDS. This well-known table identifies the frequency contents of the cardiac, respiratory and fetal sounds of interest. To those sounds should be added the Korotkoff's arterial sounds auscultated upon measuring blood pressure and mainly situated in the frequency range 20–150 Hz. Accordingly, the prior art stethoscopes designed from the information given in this table present various frequency responses comprised between 20–2000 Hz.

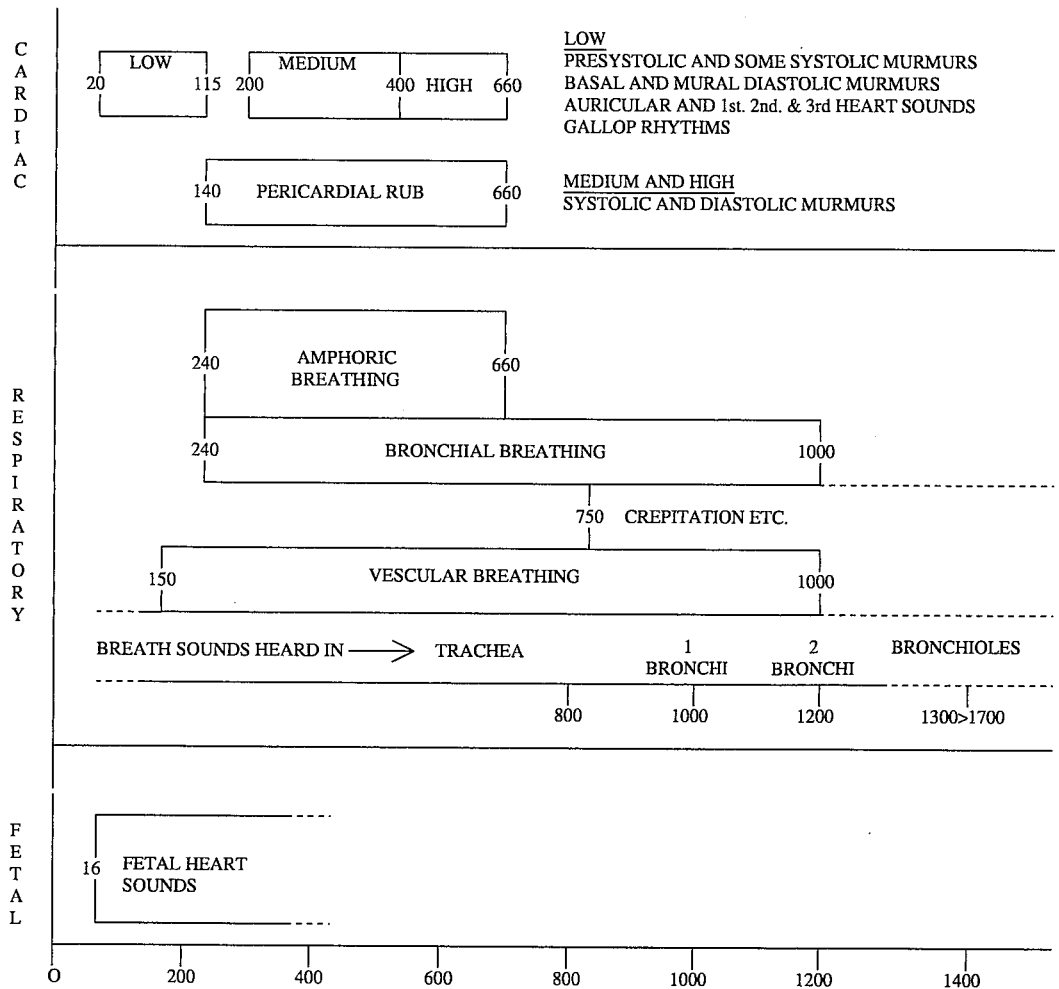

OBJECTS OF THE INVENTION

An object of the present invention is therefore to eliminate the above discussed drawback of the prior art electronic stethoscopes.

Another object of the present invention is to provide an electronic stethoscope capable of minimizing the influence of the various types of noise while optimizing auscultation of the sounds of interest.

A further object of the present invention is to provide an electronic stethoscope enabling a cardiologist to auscultate mechanical heart valves.

SUMMARY OF THE INVENTION

More specifically, in accordance with a first aspect of the present invention, there is provided an electronic stethoscope comprising first means for sensing sounds of interest produced within a patient's body and for converting these sounds to an electric signal, wherein the first means is manipulated by a user's hand, the electric signal includes low frequency noise generated by an involuntary trembling motion of the user's hand upon manipulating the first means, and the noise and sounds both have frequency components situated within a common low frequency range. A filter unit attenuates the electric signal in the common low frequency range, and comprises second means for filtering from the electric signal a substantial part of the nois& components in lower frequencies of that range, and third means for passing a substantial part of the sound components in higher frequencies of the same range. Finally, fourth means reproduces the sounds of interest in response to the electric signal from the filter unit to enable the user to hear and listen to these sounds. In accordance with preferred embodiments, (a) the common low frequency range comprises frequencies lower than 75 Hz, (b) the filter unit produces an attenuation of about 40 dB at a frequency of 30 Hz and an attenuation of about 3 dB at a frequency of 70 Hz, and (c) the filter unit comprises serially interconnected first and second high-pass filters. The first high-pass filter produces an attenuation of about 3 dB at a frequency of 60 Hz and an overshoot of about 3 dB at a frequency of 80 Hz. The second high-pass filter produces an attenuation of about 3 dB at a frequency of 80 Hz.

The present invention also relates to an electronic stethoscope comprising (a) first means for sensing sounds of interest produced within a patient's body and for converting these sounds to an electric signal, wherein the first means are capable of sensing external ambient sounds whereby the electric signal includes noise generated by those external ambient sounds, and wherein the noise and sounds both have frequency components situated within a common frequency range, (b) a filter unit for attenuating the electric signal in the common frequency range, this filter unit having a frequency response adequate to optimize both attenuation of the noise components and passing of the sound components, taking into consideration the variation of sensitivity of the human ear in function of frequency, and (c) second means for reproducing the sounds in response to the electric signal from the filter unit to enable a user to hear and listen to the sounds of interest. According to a first preferred embodiment, the electronic stethoscope can operate in a diaphragm mode and the common frequency range comprises the frequency range situated between 160 and 1300 Hz, and the filter unit comprises a low-pass filter producing an attenuation of about 3 dB at a frequency of 160 Hz and an attenuation of about 40 dB at a frequency of 700 Hz. According to a second preferred embodiment, the electronic stethoscope can operate in a bell mode and the common frequency range comprises the frequency range situated between 110 and 1300 Hz, and the filter unit comprises a low-pass filter producing a gain of about 3 dB at a frequency of 90 Hz, an attenuation of about 3 dB at a frequency of 120 Hz and an attenuation of about 40 dB at a frequency of 550 Hz.

Further in accordance with the present invention, there is provided an electronic stethoscope comprising first means for sensing sounds of interest produced within a patient's body and for converting these sounds of interest to an electric signal, wherein the sounds of interest comprise sounds produced by a mechanical heart valve having frequency components situated within a high frequency range, and second means for reproducing the sounds of interest in response to the electric signal to enable a user to hear and listen to the sounds of interest. A third filter means is interposed between the first and second means for passing the frequency components situated within the high frequency range and included in the electric signal, and a fourth means is responsive to detection of these frequency components for transmitting these components from the third filter means to the second means for reproduction of the sounds of the mechanical heart valve. Preferably, the high frequency range comprises the frequency range situated between 1.3 and 20 kHz, and the third filter means comprises a band-pass filter producing an attenuation of about 40 dB at a frequency of 2.5 kHz, an attenuation of about 20 dB between 5 and 10 kHz, and an attenuation of about 40 dB at a frequency of 30 kHz.

The present invention still further relates to an electronic stethoscope comprising first means for sensing sounds of interest produced within a patient's body and for converting these sounds of interest to an electric signal, and second means for reproducing the sounds of interest in response to the electric signal from the first means to enable a user to hear and listen to these sounds of interest, wherein third means detects the amplitude level of the electric signal for momentarily and repeatedly interrupting operation of the second means when the detected amplitude level is higher than a predetermined amplitude level threshold, whereby the second means are prevented from producing sounds of too high intensity susceptible to harm the inner ear of the user. Advantageously, the third means comprises a pulse generator for producing pulses, and an amplitude level detector for activating the pulse generator when the amplitude level of the electric signal is higher than the predetermined amplitude level threshold, the second means comprising an electric signal audio amplifier supplied with the pulses from the pulse generator and switched on and off in response to these pulses in order to reduce the level of the reproduced sounds while giving to the user the impression that the stethoscope operates.

Many of the above described characteristics of the electronic stethoscope according to the invention may be combined to provide a more efficient and versatile stethoscope.

The objects, advantages and other features of the present invention will become more apparent upon reading of the following non restrictive description of a preferred embodiment of the electronic stethoscope, given by way of example only with reference to the accompanying drawings.

BRIEF DESCRIPTION OF THE DRAWINGS

In the appended drawings:

FIG. 6 is a block diagram of the inner ear protecting unit of the electronic stethoscope of FIG. 1.

DETAILED DESCRIPTION OF THE PREFERRED EMBODIMENT

In the different figures of the appended drawings, the corresponding elements are identified by the same references.

Figure 1:
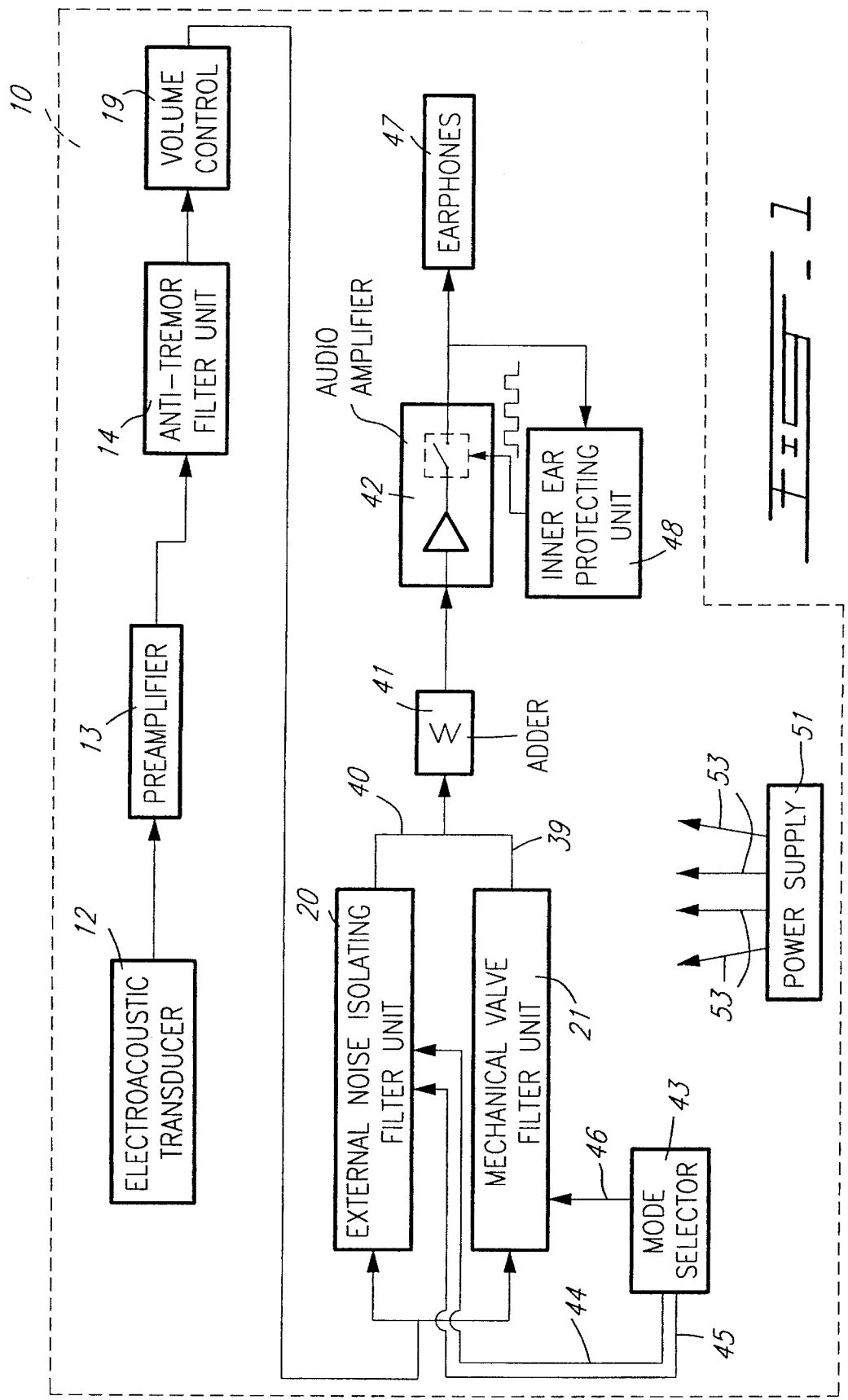
FIG. 1 is a schematic block diagram of the preferred embodiment of the electronic stethoscope in accordance with the present invention, comprising an anti-tremor filter unit, an external noise isolating filter unit, a mechanical valve filter unit, and an inner ear protecting unit.

The electronic stethoscope in accordance with the present invention is generally identified by the reference 10 in FIG. 1.

As illustrated in FIG. 1, the stethoscope 10 comprises an electroacoustic transducer (microphone) 12. The electroacoustic transducer 12 obviously forms part of a probe (not shown) of the electronic stethoscope 10, applied to the patient's body during auscultation. The electroacoustic transducer 12 is capable of sensing, when the probe is applied to the patient's body, the sounds of interest produced within the patient's body and of converting these sounds to an electric signal.

The low-level electric signal from the electroacoustic transducer 12 is amplified by a preamplifier 13 before being applied to an anti-tremor filter unit 14. As well known to those of ordinary skill in the art, the preamplifier 13 presents suitable input and output impedances and provides gain so that the low-level signal from the electroacoustic transducer 12 may be further processed without appreciable degradation in the signal-to-noise ratio.

Figure 2:
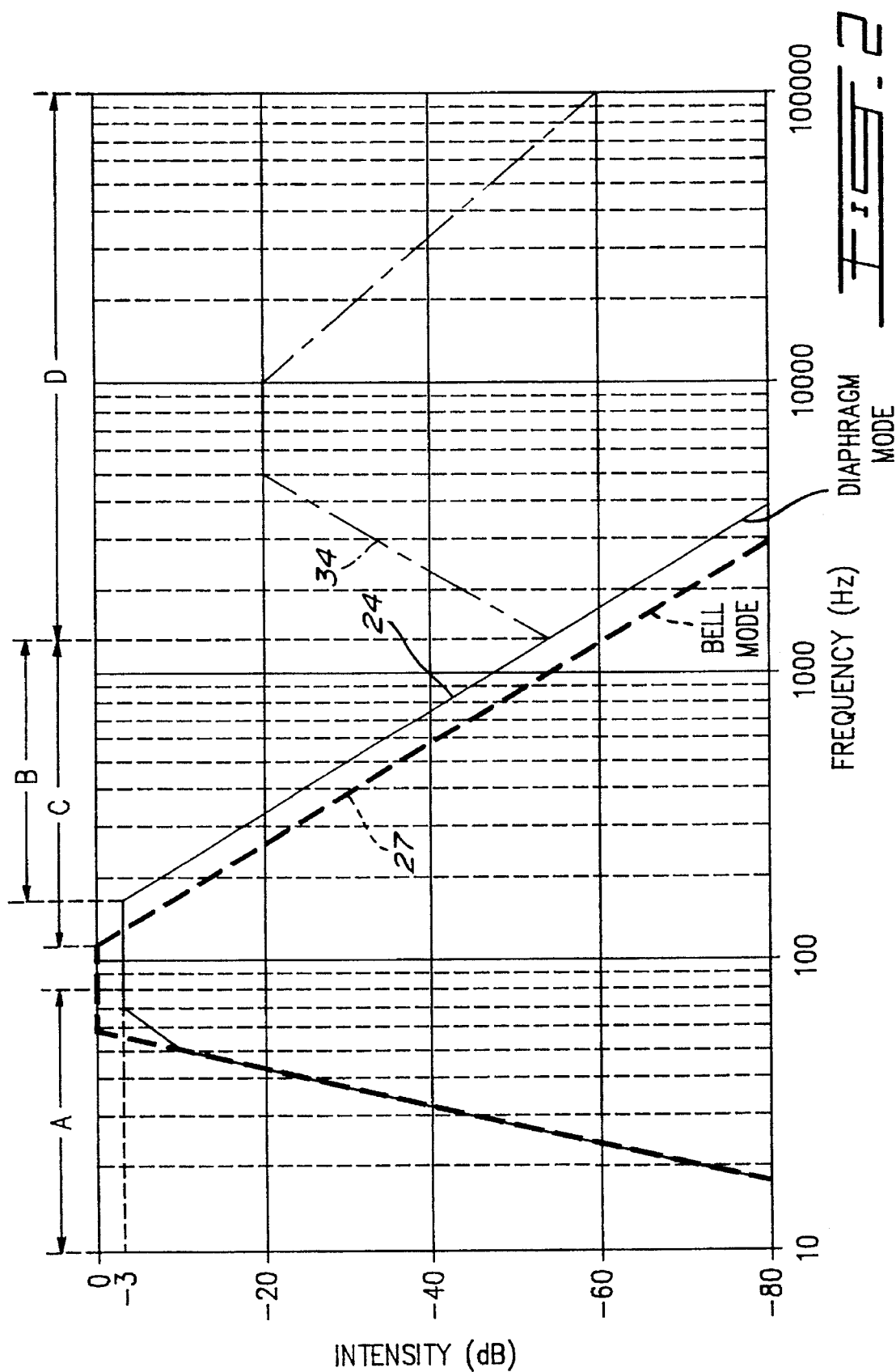
FIG. 2 is a logarithmic graph showing the frequency response of the electronic stethoscope of FIG. 1.

Referring to FIG. 2, the anti-tremor filter unit 14 attenuates the electric signal in the low frequency range including frequencies lower than 75 Hz (section A of the frequency response of FIG. 2). As indicated in the foregoing description, the frequency characteristic of the tremor is mainly situated in the frequency range 10–100 Hz, that frequency range also including low frequency heart sounds (see the above TABLE OF COMMON AUSCULTATORY SOUNDS) and the Korotkoff's sounds. Accordingly, the anti-tremor filter unit 14 should minimize the influence of the tremor while optimizing auscultation of these low frequency sounds of interest. It has been found that a high-pass filter unit adjusted to produce an attenuation of about 40 dB at a frequency of 30 Hz and an attenuation of about 3 dB at 70 Hz appropriately fulfills this dual function (see section A of the frequency response of FIG. 2).

Figure 3:
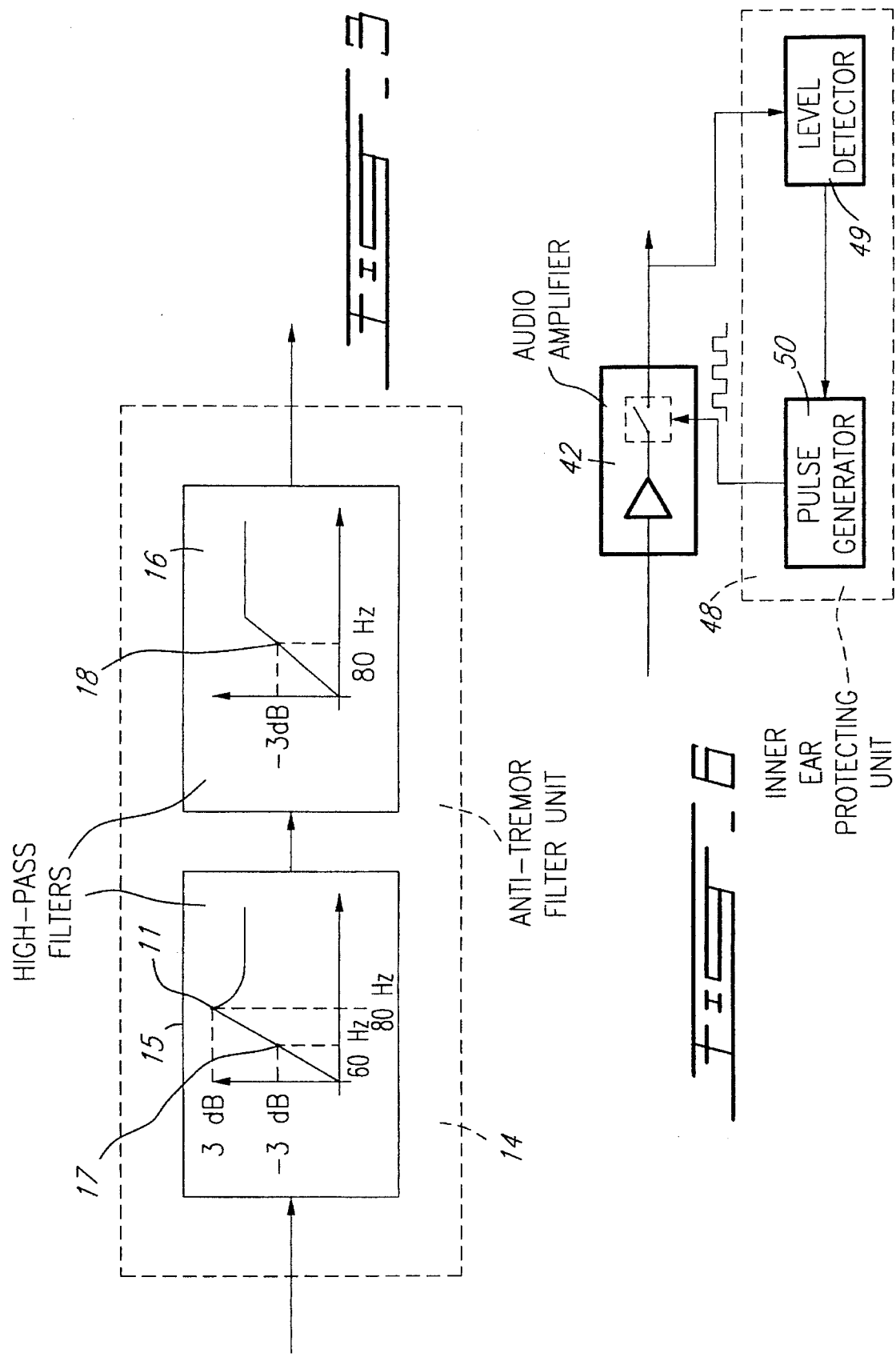
FIG. 3 is a block diagram of the anti-tremor filter unit of the electronic stethoscope of FIG. 1.

To obtain section A of the frequency response of FIG. 2, the anti-tremor filter unit 14 is formed, as shown in FIG. 3, of two serial high-pass filters 15 and 16. As illustrated, filter 15 produces an attenuation of about 3 dB at a frequency of 60 Hz (point 17 in FIG. 3) and an overshoot of about 3 dB at a frequency of 80 Hz (point 11 in FIG. 3), while filter 16 produces an attenuation of about 3 dB at a frequency of 80 Hz (point 18 of FIG. 3). Superimposition of the frequency responses of the high-pass filters 15 and 16 provides section A of the frequency response of FIG. 2. The key is that such superimposition will cut lower frequency tremor but will not affect drastically higher frequency useful signal. More specifically, filter unit 14 removes from the electric signal a substantial part of the noise components in lower frequencies of the range including frequencies lower than 75 Hz, and passes a substantial part of the sound components of interest in higher frequencies of the same range.

The filtered electric signal from the anti-tremor filter unit 14 is supplied to a volume control 19. Volume control 19 is a circuit allowing the physician to adjust the volume of the sounds reproduced by means of the stethoscope 1. For that purpose, volume control 19 will raise or lower the amplitude of the electric signal from the output of the anti-tremor filter unit 14. Volume control 19 may include an adjustable resistive element (not shown), associated or not with an amplifier (not shown) and manually actuated by the physician while manipulating the stethoscope's probe. Volume controls are well known to those of ordinary skill in the art and accordingly volume control 19 will not be further described in the present disclosure.

The electric signal from volume control 19 is supplied to an external noise isolating filter unit 20 and to a mechanical valve filter unit 21.

Figure 4:
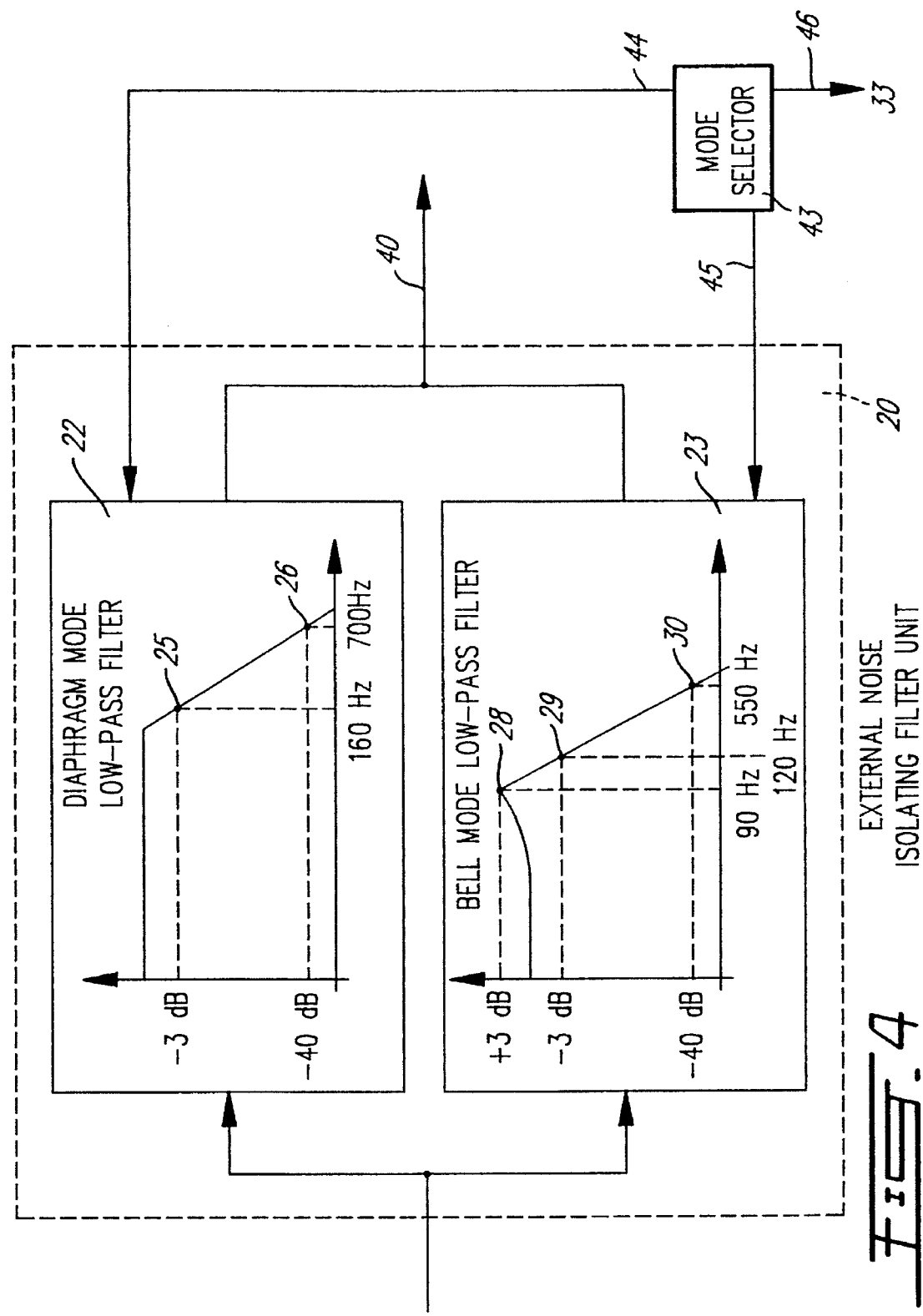
FIG. 4 is a block diagram of the external noise isolating filter unit of the stethoscope of FIG. 1.

As illustrated in FIG. 4, external noise isolating filter unit 20 comprises a diaphragm mode low-pass filter 22 and a bell mode low-pass filter 23.

Low-pass filter 22 allows the stethoscope 10 to operate in the diaphragm mode. It attenuates the electric signal in the frequency range 160–1300 Hz (curve 24 of section B of the frequency response of FIG. 2). As indicated in the foregoing description, the external noise has a frequency characteristic situated in the frequency range 300–3000 Hz. The above TABLE OF COMMON AUSCULTATORY SOUNDS also indicates that medium and high frequency heart and respiratory sounds form part of the frequency range 160–1300 Hz. Therefore, the diaphragm mode low-pass filter 22 should minimize the influence of the external noise while optimizing auscultation of the sounds of interest in the frequency range 160–1300 Hz. It has been found that a low-pass filter 22 adjusted to produce an attenuation of about 3 dB at a frequency of 160 Hz (point 25 of FIG. 4) and an attenuation of about 40 dB at a frequency of 700 Hz (point 26 of FIG. 4) appropriately fulfills this dual function (see curve 24 of section B of the frequency response of FIG. 2) while taking into consideration the above mentioned variation of sensitivity of the human ear in function of frequency. As can be seen in FIG. 2, external noise components having a frequency higher than 1300 Hz are greatly attenuated by the diaphragm mode low-pass filter 22.

Low-pass filter 23 allows the stethoscope 10 to operate in the bell mode. It attenuates the electric signal in the frequency range 110–1300 Hz (curve 27 of section C of the frequency response of FIG. 2). As indicated in the foregoing description, the external noise has a frequency characteristic situated in the frequency range 300–3000 Hz. The above TABLE OF COMMON AUSCULTATORY SOUNDS also indicates that medium and high frequency heart and respiratory sounds form part of the frequency range 110–1300 Hz. Therefore, the bell mode low-pass filter 22 should minimize the influence of the external noise while optimizing auscultation of the sounds of interest in the frequency range 110–1300 Hz. It has been found that a low-pass filter 23 adjusted to produce a gain of about 3 dB at a frequency of 90 Hz (point 28 of FIG. 4), an attenuation of about 3 dB at 120 Hz (point 29 of FIG. 4), and an attenuation of about 40 dB at a frequency of 550 Hz (point 30 of FIG. 4) appropriately fulfills this dual function (see curve 27 of section C of the frequency response of FIG. 2) while taking into consideration the above mentioned variation of sensitivity of the human ear in function of frequency. Again, FIG. 2 shows that external noise components having a frequency higher than 1300 Hz are greatly attenuated by the bell mode low-pass filter 23.

Signals from the low-pass filters 22 and 23 are supplied to a common output 40 of the external noise isolating filter unit 20.

Connected in parallel with the external noise isolating filter unit 20 is the mechanical valve filter unit 21, for enabling a cardiologist to auscultate mechanical heart valves.

The above mentioned clinical study has also brought to light the importance of enabling cardiologists to auscultate heart valvular prostheses in order to establish diagnosis. Depending on the type of prosthesis (bioprosthesis or mechanical prosthesis), certain sounds detected during auscultation can indicate serious problems.

As bioprotheses are made of biological tissue, their acoustic signature is substantially the same as that of natural valves and are located in the same frequency range. The frequency characteristics of normal and pathological sounds produced by this type of valves are consequently the same as those exposed in the section "cardiology" of the above TABLE OF COMMON AUSCULTATORY SOUNDS, in the low, medium and high frequency ranges. On the contrary, mechanical valves have acoustic signatures concentrated in the frequency range 5–20 kHz. Upon auscultating a mechanical valve, the cardiologist should hear the very high frequency "click"; the absence thereof is usually interpreted as being an abnormal situation, very serious in certain cases. For example, the absence of the "click" can result from the formation of a thrombus. Therefore, it is a requirement for an electronic stethoscope used in cardiology to enable auscultation of very high frequencies.

Figure 5:
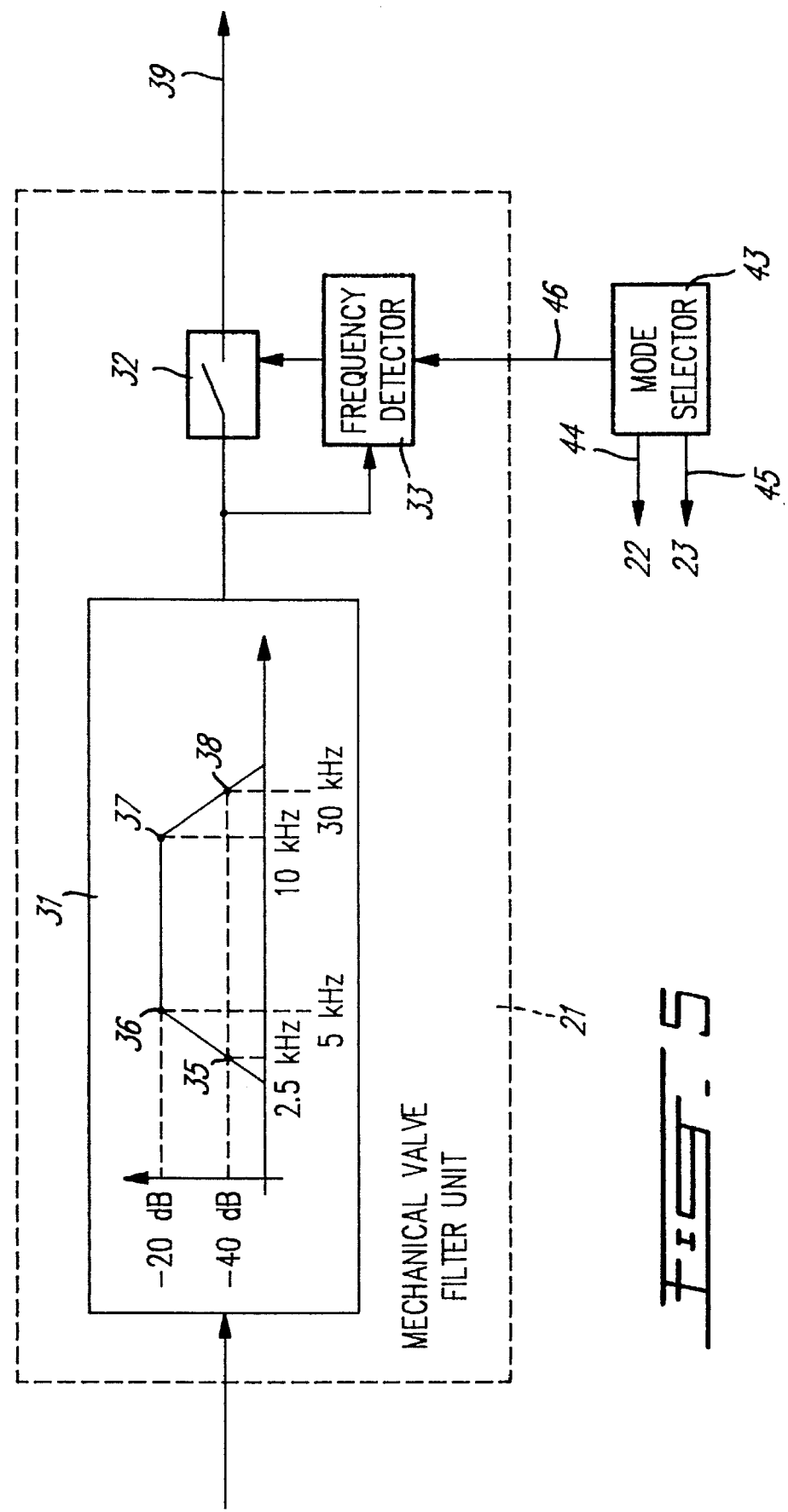
FIG. 5 is a block diagram of the mechanical valve filter unit of the electronic stethoscope of FIG. 1.

As illustrated in FIG. 5, the mechanical valve filter unit 21 comprises a band-pass filter 31, a switch unit 32 and a frequency detector 33. Filter 31 acts in the frequency range 1.3–20 kHz (see curve 34 of section D of the frequency response of FIG. 2). It has been found that a band-pass filter 31 adjusted to produce an attenuation of about 40 dB at a frequency of 2.5 kHz (point 35 of FIG. 5), and attenuation of about 20 dB in the range 5–10 kHz (section of curve between points 36 and 37 of FIG. 5), and an attenuation of about 40 dB at a frequency of 30 kHz (point 38 of FIG. 5) will allow the cardiologist to appropriately auscultate mechanical heart valves. As the sensitivity of the human ear is higher in the frequency range of 1.3–10 kHz, filter 31 provides for an attenuation of at least 20 dB over that range.

The signal from band-pass filter 31 is supplied to a frequency detector 33. When frequencies higher than 1300 Hz are present in this signal, the frequency detector 33 senses them and closes the switch unit 32 to supply the signal from the band-pass filter 31 to the output 39 of filter unit 21. Therefore, the mechanical valve filter unit 21 is active only when a given level of frequency components higher than 1300 Hz are detected whereby filter 21 eliminates any ambient or electronic noise of such frequency when the patient is not wearing a mechanical heart valve.

The signals from the output 40 of the external noise isolating filter unit 20 and from the output 39 of the mechanical valve filter unit 21 are added to each other through an adder 41 (FIG. 1) before being supplied to an audio amplifier 42.

As shown in FIGS. 1, 4 and 5, a mode selector 43 enables the physician or other medical practitioner to select the mode of operation of the electronic stethoscope 10. Mode selector 43 comprises a first output 44 to enable or disable the diaphragm mode low-pass filter 22, a second output 45 to enable or disable the bell mode low-pass filter 23, and a third output 46 to enable or disable the frequency detector 33 and thereby enable or disable the mechanical valve filter unit 21. The physician or other medical practitioner can therefore select the diaphragm or bell mode with or without the mechanical valve mode.

As a non limitative example, selection of the diaphragm mode through selector 43 could enable operation of the mechanical valve filter unit 21 when frequencies higher than 1300 Hz are present in the signal. With the diaphragm mode selected, it will be difficult for a cardiologist auscultating low frequency sounds produced by natural heart valves to concentrate on these low frequency sounds in the presence of a mechanical heart valve producing high frequency sounds of higher intensity. For a selective listening of low frequency sounds, the cardiologist can select through the mode selector 43 the bell mode which is a closed frequency range mode in which the mechanical valve filter unit 21 is inactive. Moreover, as indicated by curve 27 of FIG. 2, the bell mode accentuates the low frequencies located between 50 and 100 Hz and attenuates the medium frequencies between 100 and 1300 Hz. This additional feature enables a physician or other medical practitioner to concentrate on low frequency sounds in many situations in which medium, high and very high frequencies are present.

Referring back to FIG. 1, the signal from the adder 41 is amplified by the audio amplifier 42 and reproduced by means of earphones 47.

In order to protect the inner ear of the physician or other medical practitioner, a protecting unit 48 prevents harmonic distortion of the signal and minimizes the undesirable effects of the noise generated by preauscultation manipulations of the probe and the movements (perceptible to the human eyes) of the physician and/or patient. For that purpose, the inner ear protecting unit 48 comprises a detector 49 for detecting the amplitude level of the signal from the audio amplifier 42 and for activating a pulse generator when the signal level is higher than a given amplitude level threshold. Pulse generator 50, when activated, produces a train of pulses that switches the audio amplifier 42 on and off to reduce the amplitude level of the signal supplied to the earphones 47. Switching the audio amplifier 42 on and off also gives to the user the impression that the stethoscope operates.

A power supply 51 supplies with electric energy the various circuits of the electronic stethoscope 10, as schematically indicated by the arrows 53.

As can be appreciated, the frequency response of FIG. 2 is divided into three main sections, namely section A, section B or C, and section D respectively controlled through a corresponding dedicated filter unit. More specifically, section A is controlled by the anti-tremor filter unit 14, section B by the diaphragm mode low-pass filter 22, section C is controlled by the bell mode low-pass filter 23, and section D by the mechanical valve filter unit 21. The filter units 14, 22, 23 and 21 have been optimized with the help of specialists in different fields of the medical profession having auscultated a plurality of patients presenting various pathologies. This collaboration enabled precise definition of the specifications of the frequency response of FIG. 2.

It should be mentioned that the frequency responses, in particular the frequency bandwidth of the anti-tremor filter unit 14, the external noise isolating filter unit 20 and the mechanical valve filter unit 21 can be adjusted in function of the specialty of the user, for example cardiology, pneumology, measure of blood pressure, etc., in order to minimize the noise of biological nature which do not present interest for the specialist. The frequency response of FIG. 2 corresponds to an electronic stethoscope particularly well suited for cardiology.

The noise of electronic nature has been minimized by way of a judicious choice of electronic components providing the overall circuit with a very low level of background noise.

Although the present invention has been described hereinabove by way of a preferred embodiment thereof, this embodiment can be modified at will, within the scope of the appended claims, without departing from the spirit and nature of the invention.

What is claimed is:

1. An electronic stethoscope comprising:
   first means for sensing sounds of interest produced within a patient's body and for converting said sounds to an electric signal, wherein said first means is manipulated by a user's hand, said electric signal includes low frequency noise generated by an involuntary trembling motion of the user's hand upon manipulating the first means, and said noise and sounds both have frequency components situated within a common low frequency range;
   a filter unit for attenuating said electric signal in the common low frequency range, said filter unit comprising second means for filtering from said electric signal a substantial part of the noise components in lower frequencies of said range, and third means for passing a substantial part of the sound components in higher frequencies of said range; and
   fourth means for reproducing said sounds in response to the electric signal from the filter unit to enable the user to hear and listen to said sounds;
   wherein:
      said common low frequency range comprises the frequencies lower than 75 Hz; and
      said filter unit produced at attenuation of about 40 dB at a frequency of 30 Hz and an attenuation of about 3 dB at a frequency of 70 Hz, and comprises serially interconnected first and second high-pass filters, said first high-pass filter producing an attenuation of about 3 dB at a frequency of 60 Hz and an overshoot of about 3 dB at a frequency of 80 Hz, and said second high-pass filter producing an attenuation of about 3 dB at a frequency of 80 Hz.

2. An electronic stethoscope comprising:
   first means for sensing sounds of interest produced within a patient's body and for converting said sounds of interest to an electric signal;
   second means for reproducing said sounds of interest in response to said electric signal from the first means to enable a user to hear and listen to said sounds of interest; and
   third means for detecting an amplitude level of said electric signal for momentarily and repeatedly interrupting operation of the second means when the detected amplitude level of said electric signal is higher than a predetermined amplitude level threshold to prevent said second means from producing sounds of too high intensity susceptible to harm the inner ear of the user;
   wherein said third means comprises a pulse generator for producing pulses, and an amplitude level detector for activating said pulse generator when the amplitude level of the electric signal is higher than said predetermined amplitude level threshold, and wherein said second means comprises an electric signal audio amplifier supplied with the pulses from said pulse generator and switched on and off in response to said pulses in order to reduce the level of the reproduced sounds while giving to the user the impression that the stethoscope operates.

3. An electronic stethoscope comprising:
   first means for sensing sounds of interest produced within a patient's body and for converting said sounds of interest to an electric signal;
   second means for reproducing said sounds of interest in response to said electric signal from the first means to enable a user to hear and listen to said sounds of interest, said second means comprising an audio amplifier for amplifying said electric signal and earphones for reproducing the amplified electric signal from the audio amplifier; and
   third means for detecting an amplitude level of the amplified electric signal from the audio amplifier; and
   fourth means for momentarily and repeatedly switching the audio amplifier off when the detected amplitude level of said amplified electric signal is higher than a predetermined amplitude level threshold to prevent said earphones from producing sounds of too high intensity susceptible to harm the inner ear of the user.

4. An electronic stethoscope as recited in claim 3, wherein:
   said first means is manipulated by a user's hand, said electric signal includes low frequency noise generated by an involuntary trembling motion of the user's hand upon manipulating the first means, and said low frequency noise and sounds of interest both have frequency components situated within a common low frequency range;
   said second means comprises a filter unit for attenuating said electric signal in the common low frequency range, said filter unit comprising fifth means for filtering from said electric signal a substantial part of the noise components in lower frequencies of said range, and sixth means for passing a subetantial part of the sound components in higher frequencies of said range.

5. An electronic stethoscope as recited in claim 3, wherein:
   said first means also senses external ambient sounds whereby said electric signal includes noise generated by said external ambient sounds, said noise and sounds of interest both have frequency components situated within a common frequency range;

said second means comprises a filter unit for attenuating said electric signal in the common frequency range, said filter unit having a noise-attenuating frequency response for optimizing both attenuation of said noise components and passing of said sound components, taking into consideration the variation of sensitivity of the human ear in function of frequency.

6. An electronic stethoscope as recited in claim 3, wherein:

said sounds of interest comprise sounds produced by a mechanical heart valve having frequency components situated within a given high frequency range; and said second means comprises:

fourth filtering means interposed between said first means and said audio amplifier for passing said frequency components situated within the given high frequency range from the first means to the audio amplifier; and fifth means responsive to detection of said frequency components situated within the given high frequency range for transmitting said frequency components situated within the given high frequency range from the fourth filtering means to the audio amplifier for reproduction of the sounds of said mechanical heart valve.

\* \* \* \* \*

UNITED STATES PATENT AND TRADEMARK OFFICE
CERTIFICATE OF CORRECTION

PATENT NO. : 5,602,924

DATED : Feb. 11, 1997

INVENTOR(S) : Durand et al.

It is certified that error appears in the above-identified patent and that said Letters Patent is hereby corrected as shown below:

On the cover page, in [75] Inventors, "Grenien" should read --Grenier--.

In column 5, line 28, "nois&" should read --noise--.

In column 11, line 50, claim 1, "produced" should read --produces--.

Signed and Sealed this

Fourteenth Day of October, 1997

*Attest:*

BRUCE LEHMAN

*Attesting Officer*  *Commissioner of Patents and Trademarks*